United States Patent
Lal et al.

(10) Patent No.: US 6,870,068 B1
(45) Date of Patent: Mar. 22, 2005

(54) SYNTHESIS OF PENTAFLUOROSULFURANYL SUBSTITUTED ALKANES

(75) Inventors: Gauri Sankar Lal, Whitehall, PA (US); Kristen Elaine Minnich, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/713,230

(22) Filed: Nov. 14, 2003

(51) Int. Cl.$^7$ ............................................. C07C 309/00
(52) U.S. Cl. ........................................................ 562/824
(58) Field of Search ................................ 562/824, 821; 570/130, 131, 134, 137

(56) References Cited

U.S. PATENT DOCUMENTS

| | | | |
|---|---|---|---|
| 3,284,496 A | * | 11/1966 | Coffman ..................... 562/824 |
| 6,136,838 A | | 10/2000 | Chern et al. |
| 6,479,645 B1 | | 11/2002 | Lal et al. |

FOREIGN PATENT DOCUMENTS

| | | |
|---|---|---|
| DE | 197 48 109 A1 | 5/1999 |
| EP | 0 444 822 B1 | 9/1994 |

OTHER PUBLICATIONS

Journal of Fluorine Chem. By Nixon et al vol. 91 pp 13–18 1998.*

CA:107:23824 abs of Journal of Fluorine Chemistry by Terjeson et al 35(4) pp 653–62 1987.*

Journal of Fluorine Chem. By Winter et al vol. 66 pp. 109–116 1994.*

Journal of Fluorine Chem by Winter et al vol. 122 pp 251–253 2003.*

Journal of Fluorine Chem by Winter et al vol. 102 pp 79–87 2000.*

Samai Ayt–Mohand, et al, New and Convenient Method for Incorporation of Penta . . . , Organic Letters, 2002, pp. 3013–3015, vol. 4, 17.

R. Winter, et al, New SF5–Long Chain Carbon Systems, Inorganic Chem., J. of Fluo. Chem., 2001, 107, pp. 23–30.

Dieter Lentz, et al, The—SF5,—SeF5, and—TeF5 Groups in Organic Chem., Chem. of Hypervalent Compounds, 1999, Wiley–VCH, Inc., pp. 295–325.

Rolf Winter, et al, Functionalization of Pentafluoro–.., Amer. Chem. Soc., 1994, pp. 128–147.

* cited by examiner

*Primary Examiner*—Paul A. Zucker
(74) *Attorney, Agent, or Firm*—Geoffrey L. Chase

(57) ABSTRACT

Addition of an $SF_5$ group to organic compounds such as alkyl-substituted terminal alkenes, internal alkenes and cycloalkenes via the reaction with $SF_5Br$ is effected under liquid phase conditions and generally in the presence of a free radical initiator, preferably triethyl borane.

21 Claims, No Drawings

SYNTHESIS OF PENTAFLUOROSULFURANYL SUBSTITUTED ALKANES

BACKGROUND OF THE INVENTION

The development of synthetic methodologies for the introduction of sulfurpentafluoride or pentafluorosulfuranyl groups ("$SF_5$") into organic compounds has been pursued with a considerable degree of interest. The $SF_5$ groups impart unique properties to these organic compounds that include, inter alia, low surface energy, high chemical resistance, high thermal stability, high electronegativity, hydrophobicity, and high dielectric constant. The high electronegativity value of the $SF_5$ group, 3.62 on the Pauling scale, and its greater electron withdrawing ability makes it an attractive alternative for the trifluoromethyl group ("$CF_3$") found in many commercial products.

Organic compositions containing $SF_5$ have been used in a variety of applications. For example, pentafluorosulfuranyl fluoroaliphatic compositions have been used as surfactants, mono and bis (pentafluorosulfur)-substituted diacetylenes have been used to prepare $SF_5$-containing polymers, sulfur pentafluorophenyl pyrazoles have been suggested for the control of ecoparasitic infections, and sulfurpentafluoride derivatives have been used to prepare liquiderystal media. Thus, there is an interest in efficient methods for the introduction of the $SF_5$ group into a variety of compounds.

The following articles and patents are representative of methods for introducing $SF_5$ groups into organic compounds.

U.S. Pat. No. 4,535,011 discloses a process for producing mono (pentafluorosulfur diacetylene polymers wherein sulfur pentafluoro bromide is first reacted with acetylene at temperatures below about −70° C., and then, the resulting intermediate debrominated. Dehydrobromination is effected by reacting the intermediate adduct with a strong base, e.g., potassium hydroxide.

U.S. Pat. No. 6,479,645 discloses methods for producing sulfurpentafluoride compounds having a substituted silyl group. In the disclosed process, sulfur pentafluoro bromide is reacted with a trisubstituted silyl acetylene in the presence of potassium fluoride at room temperature. Bromine is removed from the intermediate compound by addition of powdered potassium hydroxide.

The article, *New and Convenient Method for Incorporation of Pentafluorosulfanyl ($SF_5$) Substituents Into Aliphatic Organic Compounds*, Samai Ayt-Mohand and W. Dolbier, Organic Letters, 2002, 4,17, 3013 discloses the addition of the $SF_5$-group to organic compounds by the reaction of $SF_5Cl$ with alkynes and alkenes in the presence of triethylborane and hexane solvent at temperatures from −30° C. to room temperature.

In the article, *New SF5-Long Chain Carbon Systems*, R. Winter and G. L. Gard, Inorganic Chemistry, Journal of Fluorine Chemistry, 107 (2001) 23–30, sulfur pentafluoro chloride is reacted with a terminal olefin, e.g., 1-hexene and 9-decyl-1-acetate to produce an intermediate in the formation of $SF_5$-terminated perfluoroalkyl thiols. The authors note that the reaction of sulfur pentafluoro bromide is too reactive with 1-hexene and only BrF adducts are found by GC analysis.

In the article, The —$SF_5$, $SeF_5$, and $TeF_5$ *Groups In Organic Chemistry*, D. Lentz and K. Seppelt, Chemistry of Hypervalent compounds© 1999 Wiley-VCH, Inc, p. 295–325, there is disclosed the addition of the $SF_5$ group into organic compounds by reaction with $S_2F_{10}$, $SF_5OF$, $SF_5Cl$, and $SF_5Br$. Successful addition of $SF_5Br$ to alkynes and fluoroalkenes was reported. It was reported also that $SF_5Br$ added in cases where $SF_5Cl$ failed and $SF_5Cl$ added in cases where $SF_5Br$ did not.

The article, *Functionalization of Pentafluoroe-$\lambda^6$-Sulfanyl ($SF_5$) Olefins and Acetylenes*, Winter and Gard, et al, American Chemical Society, ©1994 128–147 discloses the preparation of $SF_5$ derivatives of alkynes and alkenes. In one example $SF_5X$ addition to alkenes can be moderated by working either in the gas phase, (ethylene and $SF_5Br$), operating at low temperatures (−110° C.) or the reaction carried out at high dilution in an inert solvent.

BRIEF SUMMARY OF THE INVENTION

It has been discovered that one can improve the addition of the $SF_5$ group to organic compounds such as alkyl-substituted terminal alkenes, and effect addition of the $SF_5$ group to internal alkenes and cycloalkenes via reaction with $SF_5Br$. The improvement in the addition process for reaction with a terminal olefin comprises condensing $SF_5Br$ in the terminal olefin and effecting the reaction of $SF_5Br$ with under liquid phase conditions. For terminal, internal, and cyclic olefins, $SF_5Br$ is condensed in the olefin and the reaction carried out under liquid phase conditions in the presence of a free radical initiator, preferably triethyl borane. In addition, the invention relates to compositions incorporating the $SF_5$ group and Br group across the double bond of an internal or cyclic olefin. Processes for producing the resulting compositions have been, heretofore, unknown. The resulting pentafluorosulfuranyl halo substituted aliphatics can be converted to pentafluorosulfuranyl substituted aliphatics by effecting dehydrohalogenation or dehalogentation.

Generally, several advantages can be achieved by this process and these include:

an ability to incorporate the $SF_5$ group into terminal alkenes in improved yield, particularly those which do not have substituent electron withdrawing groups, in high yield; and, an ability to reduce byproduct formation due to BrF addition across the double bond and loss of reactant $SF_5Br$.

DETAILED DESCRIPTION OF THE INVENTION

Addition of an $SF_5$ group to an olefin allows for the production of many intermediates which are useful in organic synthesis. Heretofore, successful addition of the $SF_5$ group to terminal alkenes by reaction with $SF_5Br$ has been limited to those alkenes bearing electron withdrawing groups such as F, Cl, Br, $SiR_3$ and COOEt. Reaction of $SF_5Br$ with unsubstituted terminal alkenes has largely resulted in the addition of F and Br across the double bond either instead of, or in addition to, the desired addition of the $SF_5$ group and the Br group across the double bond. Reaction of $SF_5Br$ with internal olefins has either met with F and Br adding across the double bond or there has been no reaction.

The improved processes for reaction with an olefin described herein employs the reactant, $SF_5Br$ as the means for effecting the addition of the $SF_5$ group to such olefinic compounds and particularly those olefinic compounds heretofore not amenable to addition of the $SF_5$ group and Br across the double bond. In a first embodiment of the improved process, the reaction is carried out under liquid phase conditions and, as a second embodiment the reaction of $SF_5Br$ with the olefin is carried out in the presence of a free radical initiator, preferably triethyl borane.

The olefins suited for reaction with $SF_5Br$ include terminal alkenes, internal olefins and cycloalkenes. Representative terminal olefins are represented by the structure:

A wherein R' and R" are separately H, $C_{1-20}$, preferably $C_{3-12}$ alkyl or substituted alkyl, aryl or alkyl substituted aryl, $C_{1-10}$ alkoxy, $C_{1-10}$ alkyl ether, or alkenyl. Representative substituents on or within the alkyl group include heteroatoms such as O, S, N or halogen atoms such as Cl, Br, and F. Other specific groups include $OCH_3$, $-CH_2OCH_2-$, $SCH_3$, $-CH_2S-CH_2-$, $N(CH_3)_2$, $-CH_2N(CH_3)CH_2-$, $CH_2Cl$, $-CH_2CH_2Cl$, etc. Specific terminal olefins such as $C_3$ to $C_{12}$ alkenes, e.g., propylene, isobutylene, pentene, hexene, heptene, octene, decene, and dodecene, cyclic olefins such as 4-vinyl-1-cyclohexene, and aryl olefins such as styrene, and divinyl benzene. Nonconjugated dienes such as 1,4-pentadiene, 1,4-hexadiene, 1,5-hexadiene and 1,4-heptadiene, 1,5-heptadiene, 1,6-heptadiene can also be reacted.

The resulting pentafluorosulfuranyl bromo alkane compounds are represented by the structure:

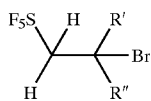
B

Internal aliphatic olefins, have been the most difficult to effect addition of the $SF_5$ group and Br across the double bond. Too often, no reaction occurs. By that it is meant only Br and F add across the double bond. By operating under liquid phase conditions and facilitating the reaction by the use of a free radical initiator, preferably one that is activated at low temperatures, e.g. below 0° C., one can add $SF_5$ and Br using $SF_5Br$ as the reactant. Internal olefins suited for the reaction are represented by the structure:

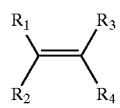
C wherein $R_1$, $R_2$, $R_3$, $R_4$ are $C_{1-12}$ alkyl, preferably $C_{1-8}$, or substituted alkyl, aryl or substituted aryl, alkoxy, alkyl ether, alkyl ester and nitrile, with $R_2$ and $R_4$ additionally being=H or halogen atoms, e.g., F, Cl and Br. Representative substituents on or within the internal olefin can include heteroatoms such as O, S, N or halogens, such as $OCH_3$, $-CH_2OCH_2-$, $SCH_3$, $-CH_2S-CH_2-$, $N(CH_3)_2$, $-CH_2N(CH_3)CH_2-$, $-CH_2Cl$, $-CH_2CH_2Cl$, etc. Where isomers of the olefins exist, e.g., in the form of cis and trans,—forms, such olefins can be used as a reactant. Representative compounds include butene, pentene, hexene, heptene, octene, nonene, dodecene and the like where the olefinic bond is internal and not terminal. Substituted examples of internal alkenes include 2-halo-2-butene, 2,3-dihalo-2-butene, 2-alkoxy-2-butene, 2,3-dialkoxy-2-butene, 2-dialkylamino-2-butene, 2,3-(bis)dialkylamino-2-butene, 2-thioalkyl-2-butene, and 2,3-(bis)thioalkyl-2-butene etc.

Compounds resulting from the addition of $SF_5Br$ to an internal olefin are represented by the structures:

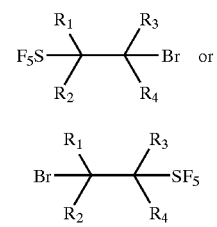
D

E

Another category of olefins include the cycloaliphatic olefins represented by the formula:

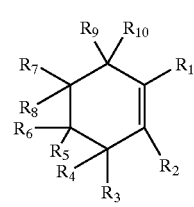
F wherein $R_1-R_{10}$=H, halogen atoms, alkyl or substituted alkyl, aryl or substituted aryl. Substituents include heteroatoms such as O, S, N or halogens $R_9$, $R_{10}$ or $R_3$, $R_4$ may be a carbonyl group (=O); $R_9$ or $R_{10}$ and $R_4$ or $R_3$ may be linked together, i.e., bridged bicyclic compounds; $R_7$ or $R_8$ and $R_5$ or $R_6$ may be linked together as in fused ring bicyclic or tricyclic cycloaliphatic or aromatic compounds. Representative cyclic olefins include: cyclohexene, cyclooctene, norbornene, dihydronaphthalene, dihydroanthracene, dihydrophenanthrene, octahydronaphthalene, dodecahydroanthracene, dodecahydrophenanthrene and the like.

Compounds produced by the reaction of $SF_5Br$ with the above cycloaliphatic olefins are represented by the structures:

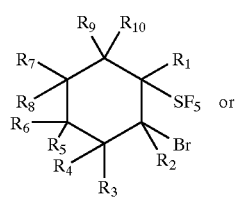
G

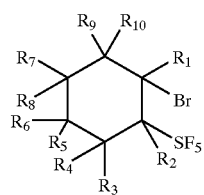

The last class of olefinic compounds are the cycloaliphatic dienes which are represented by the formula:

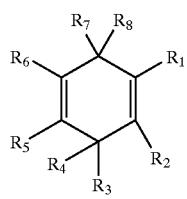

wherein $R_1$–$R_8$=H, halogen atoms, alkyl or substituted alkyl, aryl or substituted aryl. Substituents include heteroatoms such as O, S, N or halogen atoms, e.g., F, Br, and Cl; $R_7$ or $R_8$ and $R_4$ or $R_3$ may be linked together, i.e., bridged bicyclic compounds $R_7$ or $R_8$ and $R_5$ or $R_6$ may be linked together as in, fused ring bicyclic or tricyclic cycloaliphatic. The dienes may be used as long as the olefinic bonds are not conjugated. This also includes the situation where the bonding is carbonyl. Representative dienes include: 1,4-cyclohexadiene, 1,6hexahydronaphthalene, 9,13-tetrahydroanthracene and unconjugated dienes in other cycloaliphatic ring of ring size $C_5$–$C_{10}$.

The pentafluorosulfuranyl bromo aliphatic compounds are represented by the structures:

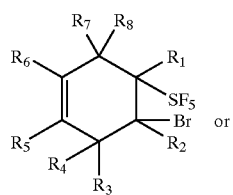

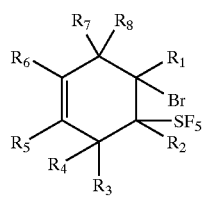

The reaction stoichiometry involving the reaction of $SF_5Br$ with an olefin is generally consistent with the level of $SF_5$ addition desired. Typically the reaction stoichiometry employs an equivalent or slight excess of $SF_5Br$ reactant, e.g., from about 1 to 1.2 moles $SF_5Br$ per mole of olefin bond.

The ability to achieve enhanced addition of the $SF_5$ group into internal and cyclic olefins without effecting substantial addition of Br and F across the double bond resides in effecting the reaction in the presence of a free radical initiator such as trialky boranes, e.g., tripropyl borane, and particularly triethylborane. Other free radical initiators include azo compounds, organic peroxides, e.g. benzoyl peroxide and t-butylhydroperoxide, and UV light. Low temperature initiation Is preferred to prevent the formation of polymerization byproducts.

The free radical initiator, e.g., triethylborane is added in an amount of 1–25 mol %, preferably 5–10 mol %, per mole of the olefin to be treated. Triethyl borane Is the preferred initiator in view of its reactivity at low temperatures, e.g., as low as –78° C.

The reaction can be carried out in a wide range of liquid mediums, i.e., the reaction can be carried out in the presence of olefin neat or it can be carried out in the presence of solvents. Representative solvents suited for carrying out the reaction include hydrocarbons, fluorocarbons, nitrites, ethers, and halocarbons. Solvent levels of from 10 to 100% by weight of the olefin can be used.

The reaction of $SF_5Br$ with the olefins is carried out at temperatures below the decomposition of $SF_5Br$, but above the activation temperature for the free radical initiator. The advantage of triethyl borane as a free radical initiator is that it is active at a low temperature, from about –90° C. to the boiling point of solvent or olefin, preferably low temperatures from –80 to +50° C., and most preferably from about –75° C. to 0° C. In the process, the $SF_5Br$ reactant is condensed into the reaction medium, and then the reaction carried out under liquid phase conditions.

Recovery of the product can be accomplished by conventional methods and these include distillation and chromatography. An advantage of using $SF_5Br$ to $SF_5Cl$ is that the bromine atom facilitates removal of the halogen atom from the thus formed product. Removal can be effected by addition of a strong base, e.g., potassium hydroxide, HBr being eliminated. Br can also be replaced by H through the use of reducing agents, e.g., tin hydrides. As a result there is an easy mechanism for the production of pentafluorosulfuranyl aliphatics via $SF_5Br$ addition with a variety of olefins.

The following reactions are representative embodiments of the described process:

Liquid Phase $SF_5Br$ Addition to Terminal Olefin

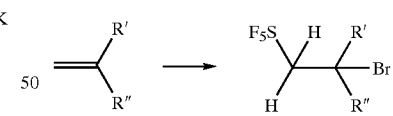

Catalyzed $SF_5Br$ Addition to Internal Olefins and to the Resulting Compositions

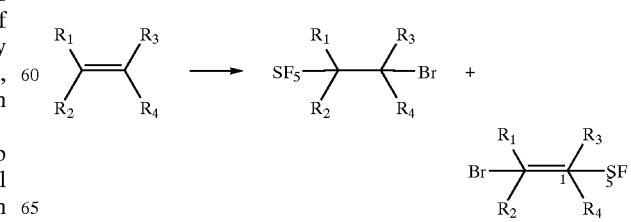

Catalyzed SF₅Br Addition to Cycloalkenes

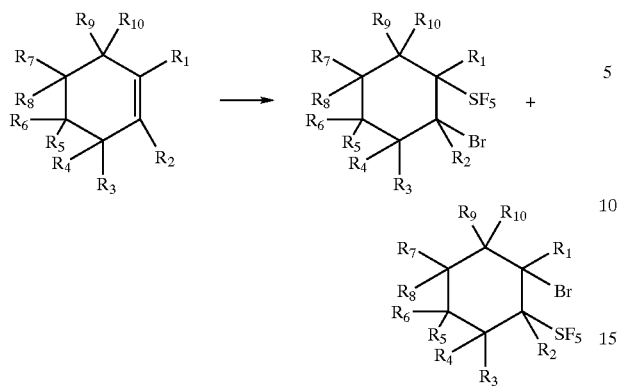

Catalyzed SF₅Br Addition to Cycloalkyldienes

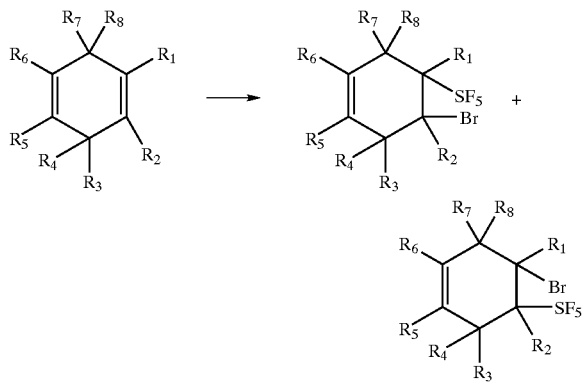

In the above reaction with cycloalkyldienes, SF₅Br can be added to one or both double bonds depending upon the reaction stoichiometry and conditions.

The following examples are intended to represent various embodiments of the invention and are not intended to restrict the scope thereof.

General Procedures

A. Uncatalyzed, Liquid Phase SF₅Br Addition to Alkenes

The alkene (2 mmole), pentane solvent (10 mL) and potassium fluoride (5 mmole) were charged to an FEP tube fitted with an inlet valve and a relief valve. The solution was cooled to −78° C. and degassed. SF₅Br (2 mmole) was then condensed into the solution. The temperature was maintained at −78° C. for one hour, and then, the solution was allowed to warm to room temperature. After 30 minutes the reactor was vented and purged with N₂. The reaction mixture was slowly added to a cold sodium bicarbonate solution. The organic layer was isolated and the products were analyzed by GC, GC/MS and NMR.

B. Catalyzed, Liquid Phase SF₅Br Addition to Alkenes

The alkene (2 mmole), pentane solvent (10 mL), potassium fluoride (5 mmole) and triethylborane (0.2 mmole, 1 M in hexane) were charged to an FEP tube fitted with an inlet valve and a relief valve. The solution was cooled to −78° C. and degassed. SF₅Br (2 mmole) was then condensed into the solution. The temperature was maintained at −78° C. for one hour, and then, the solution was allowed to warm to room temperature. After 30 minutes the reactor was vented and purged with N₂. The reaction mixture was slowly added to a cold sodium bicarbonate solution. The organic layer was Isolated and the products were analyzed by GC, GC/MS and NMR.

EXAMPLE 1

Reaction Of SF₅Br with Terminal Olefins

Terminal olefins were reacted with SF₅Br using procedure A described above. The GC area % results are shown in Table 1.

TABLE 1

GC Area % for the Uncatalyzed, Liquid Phase Reaction of SF₅Br with Terminal Olefins.

| | Alkene | Temp (° C.) | Catalyst | SF₅Br Addition |
|---|---|---|---|---|
| 1 | $H_2C=CH(CH_2)_5CH_3$ 1-Octene | −78 −78 | None Et₃B | 79 100 |
| 2 | $H_2C=CHCH_2OCH_2$—(epoxide) Allylglycidyl ether | −78 | None | 98 |
| 3 | $H_2C=CH(CH_2)_2CH=CH_2$ 1,5 Hexadiene | −35 | None | 70 12 2-SF5 |

Characterization of the SF₅Br Addition Products:

1. 1-Pentafluorosulfanyl-2-bromo octane MW=276. GC/MS m/z=277, 275, 239, 127, 111, 89, 69,57. ¹H NMR δ 0.9, (t, 3H), 1.3 (m, 6H), 1.4 (m, 1), 1.5 (m, 1H), 1.8 (m, 1H), 2.0 (m, 1H) 4.0 (m, 1H), 4.1 (m, 1H), 4.4 (m, 1H) 19F NMR δ 65 d, 82 pent.

2 1-Pentafluorosulfanyl-2-bromo glycidyl ether MW=321. GC/MS m/z =249, 247, 141, 139, 127, 113, 89, 87, 57. ¹⁹F NMR δ 65 d, 82 pent.

3 1-Pentafluorosulfanyl-2-bromo-5- hexene MW=289. GC/MS m/z=290, 286, 208, 206, 161, 163, 127, 122, 120, 89, 81. ¹H NMR δ 1.9, (t, 1H), 2.1 (m, 1H), 2.2 (m, 1), 2.3 (m, 1H), 4.0 (m, 1H), 4.2 (m, 1H) 4.4 (m, 1H), 5.1 (dd, 2H), 5.8 (m, 1H) 19F NMR δ 65 d, 82 pent.

Double Addition product GC/MS m/z =496,418,417, 289, 287,181,179,127, 119,99,89,59

The results in Table 1 show that the addition of the SF₅ group to a terminal olefin can be effected by condensing SF₅Br in the olefin and carrying out the reaction in the liquid phase. Yields can be improved in many cases where unsubstituted olefins or where the olefin has more than one double bond by the use of a free radical catalyst, e.g., triethyl borane. This is surprising in view prior art reports that SF₅Br is too reactive and only Br—F adducts are formed when using SF₅Br as a reactant. The prior art suggested the reactions, if they were to proceed, must be carried out either at gas phase conditions, at low temperatures (−110° C.) or at high dilution in an inert solvent. Where functional groups are present, e.g., a glycidyl ether, greater yields can be produced. However, as the results show in the case of reaction with hexadiene, SF₅ adds to the first double bond but SF₅ addition is dramatically reduced once addition to the terminal olefinic bond has been accomplished. Yield of SF₅ can be increased across both of the double bonds by the use of a low temperature free radial initiator.

EXAMPLE 2

Catalyzed And Uncatalyzed, Liquid Phase Reaction of Internal Olefins with $SF_5Br$ Internal olefins were reacted with $SF_5Br$ using either procedure A and B described above. The GC area % results are shown in Table 2.

TABLE 2

GC Area % for the Reaction of $SF_5Br$ with Internal Olefins.

| Alkene | | Temp (° C.) | Catalyst | $SF_5Br$ Addition |
|---|---|---|---|---|
| 4 | $CH_3CH_2CH=CH(CH_2)_2CH_3$ | −78 | $Et_3B$ | 86 |
|   | Cis 3-Heptene | −78 | None | 0 |
| 5 | $CH_3CH_2CH=CH(CH_2)_2CH_3$ | −78 | $Et_3B$ | 73 |
|   | Trans 3-Heptene | −78 | None | 50 |
| 6 | $CH_3(CH_2)_2CH=CH(CH_2)_2CH_3$ | −78 | $Et_3B$ | 91 |
|   | Trans 4-Octene | −78 | None | 0 |

Characterization of the $SF_5Br$ Addition Products:

4 3-Pentafluorosulfanyl-4-bromo heptane and 3-bromo-4-pentafluorosulfanyl heptane Mw=305. GC/MS m/z=177, 175, 137, 135, 127, 97, 89, 69, 55. $^{19}F$ NMR δ 60 t, 86 pent.

5 3-Pentafluorosulfanyl-4-bromo heptane and 3-bromo-4-pentafluorosulfanyl heptane Mw=305. GC/MS m/z=177, 175,137,135, 127, 97, 89, 69,55. $^{19}F$ NMR δ 58 t, 60 t, 86 pent.

6 4-Pentafluorosulfanyl-5-bromo octane, Mw=319. GC/MS m/z=193, 191, 127, 111, 89, 69, 55.

The results in Table 2 show that unlike the terminal olefins in Example 1, the uncatalyzed, liquid phase reaction of $SF_5Br$ with an olefin, where the olefinic bond is internal, is either ineffective in many cases or yields are low, e.g., 50%, depending upon the isomer structure. When a free radical initiator is used to catalyze the liquid phase reaction, e.g., triethyl borane, addition of the $SF_5$ group can be, yields are increased dramatically. Byproduct formation, i.e., products where there is BrF addition across the double bond are minimized.

EXAMPLE 3

Catalyzed and Uncatalyzed Reaction of $SF_5Br$ with Cycloalkenes

Cycloalkenes were reacted with $SF_5Br$ using procedures A and B described above. The GC area % results are shown in Table 3.

TABLE 3

GC Area % for the Reaction of $SF_5Br$ with Cycloalkenes.

| | Alkene | Temp (° C.) | Catalyst | $SF_5Br$ Addition |
|---|---|---|---|---|
| 7 | Cyclohexene | −78 | $Et_3B$ | 91 |
|   |  | −78 | None | 48 |
| 8 | 3-Bromo-1-Cyclohexene | −78 | $Et_3B$ | 50 |
|   |  | −78 | None | 5 |
| 9 | 4-Vinyl-1-Cyclohexene | −78 | $Et_3B$ | 34 1-SF5 + 55 2-$SF_5$ |
|   |  | −78 | None | 56 |
| 10 | 2-Cyclohexen-1-one | −78 * | $Et_3B$ | 34 |
|    |  | −78 * | None | 0 |

* Reaction did not go to completion.

Characterization of the $SF_5Br$ Addition Products:

7 1-Pentafluorosulfanyl-2-bromo cyclohexane Mw=289. GC/MS m/z=290, 288, 209, 127, 101, 89, 81. $^1H$ NMR δ 1.3, (m, 2H), 1.6 (m, 2H), 1.8 (m, 1H), 2.1 (m,1H), 2.2 (m,2H), 2.4 (m, 1H) 4.3 (m, 1H), 4.9 (d, 1H) $^{19}F$ NMR δ 57 d, 85 pent.

8 1-Pentafluorosulfanyl-2, 3-dibromo cyclohexane Mw=368 GC/MS m/z=368, 288, 207, 181, 179, 161, 159, 127, 99, 89, 79.

9 Mw=316 GC/Ms m/z=316, 314, 235,189, 187, 127, 107, 89, 79.

Double addition product Mw=523. GC/MS m/z=315, 313, 253, 207, 205, 187, 185, 145, 127, 105, 79.

10 3-Pentafluorosulfanyl-2-bromo cyclohexanone Mw=303. GC/MS m/z=302, 300, 177, 175, 149, 147, 127, 121, 119, 89, 67.

The results in Table 3 show that, at best, the uncatalyzed liquid phase reaction of cycloalkenes results in a poor yield of $SF_5$ addition product. The yield of $SF_5$ products is increased by the addition of a radical initiator. Where there is a substituent on the cycloaliphatic ring, e.g., a halogen such as Br or a carbonyl group a free radical catalyst is necessary to achieve reaction in a significant amount.

EXAMPLE 4

Catalyzed and Uncatalyzed Reaction of $SF_5Br$ with Cycloalkadienes

Cycloalkadienes were reacted with $SF_5Br$ using procedures A and B described above. The GC area % results are shown in Table 4.

TABLE 4

GC Area % for the Reaction of SF₅Br with Cycloalkadienes.

| | Alkene | Temp (° C.) | Catalyst | SF₅Br Addition |
|---|---|---|---|---|
| 11 | 1,3 Cyclohexadiene | −78 | Et₃B | — |
| 12 | 1,4 Cyclohexadiene | −78<br>−78 **<br>−78 | Et₃B<br>Et₃B<br>None | 97<br>28 1-SF₅ + 43 2-SF₅<br>36 |

** two equivalents SF₅Br added to the reaction.

Characterization of the SF₅Br Addition Products:

12 1-Pentafluorosulfanyl-2-bromo- 4-cyclohexene Mw=287. GC/MS m/z=288, 286, 207, 161, 159, 127, 99, 89, 79. $^1$H NMR δ 2.6, (d, 1H), 3.0 (dt, 3H), 4.4 (m, 1H), 5.0 (m,1H), 5.7 (m,2H) $^{19}$F NMR δ 55 d, 84 pent.

The results in Table 4 show the position of the double bond is important. When the double bond is not conjugated, high yields of SF₅ addition can be achieved when a free radical initiator is employed. If the bonds are conjugated, yields of SF₅ are low even when a free radical initiator is employed.

EXAMPLE 5

Catalyzed and Uncatalyzed Reaction of SF₅Br with Norbornene

Norbornene was reacted with SFrBr using procedures A and B described above. The GC area % results are shown in Table 5.

TABLE 5

GC Area % for the Reaction of SF₅Br with Norbornene.

| | Alkene | Temp (° C.) | Catalyst | SF₅Br Addition |
|---|---|---|---|---|
| 13 | Norbornene | −78<br>−78 | Et₃B<br>None | 98<br>— |

Characterization of the SF₅ Containing Products:

13 1-Pentafluorosulfanyl-2-bromo norbornane Mw=301. GC/MS m/z=223, 221, 175, 173, 127, 113, 93, 89, 67.

The results in Table 5 show bicyclic molecules containing a double bond show high yields of SF₅ addition when a radical catalyst is employed in the reaction with SF₅Br.

Summarizing the examples, it can be seen that reaction of SF₅Br with terminal olefins can provide reasonably good yields when the reaction is carried under liquid phase conditions and SF₅Br is condensed into the reaction medium. Low temperature conditions facilitates the condensation reaction. When the reaction is carried out in the presence of a free radical initiator, yields are increased, particularly in those cases where the terminal olefin is unsubstituted.

Heretofore, there have been no reports of the successful addition of SF₅ groups to Internal and cyclic olefins by reaction with SF₅Br. Even when the reaction is carried out under liquid phase conditions and the SF₅Br is condensed into the olefin, very poor to moderate yields of SF5Br addition are achieved. And, isomer structure is a factor as to whether the reaction proceeds. The results in Tables 2 and 3 also show that the addition of a free radical initiator to the reaction medium in an amount preferably from 5 to 10 mole % significantly enhances the yield of products containing SF₅ group.

Dienes can be reacted with SF₅Br by employing a free radical initiator. To achieve more than one SF₅ group onto the diene, it is necessary to use a free radical initiator.

Although not intending to be bound by theory, it has generally been viewed that SF₅Br is too reactive with olefinic molecules resulting in Br—F addition. It is surprising that the addition of a radical catalyst enhances the selectivity for SF₅ addition instead of the customary BrF addition. The mechanism for SF₅Br reactions is by and large believed to be free radical in nature. Some experiments, however, suggest SF₅Br reacts through an electrophilic mechanism which results in Br—F addition as the major product. By adding the radical initiator it is believed that we are shifting the mechanism toward the radical pathway as opposed to electrophilic addition, thereby resulting in increased SF₅ addition. Surprisingly, then, by carrying out the reaction, liquid phase, in the presence of a free radical initiator, one changes the reaction mechanism such that SF₅ and Br add across the double bond rather than F and Br adding across the double bond.

What is claimed is:

1. A process for adding an SF₅ group and Br atom to a terminal alkene of the formula:

to produce a compound represented by the structure:

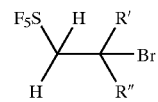

wherein R' and R" are separately H, C$_{1-20}$, alkyl or substituted alkyl aryl or alkyl substituted aryl, C$_{1-10}$ alkoxy, C$_{1-10}$ alkyl ether, alkenyl, alkyl halogen, alkyl thionyl and alkyl amino, which comprises:
condensing SF₅Br in said terminal alkene and, then, reacting of said terminal alkene with SF₅Br under liquid phase conditions.

2. The process of claim 1 wherein the terminal alkene is selected from the group consisting of propylene, isobutylene, pentene, hexene, heptene, octene, decene, dodecene, 4-vinyl-1-cyclohexene, styrene, divinyl benzene and dienes selected from the group consisting of 1,4-pentadiene, 1,4-hexadiene, 1,5-hexadiene and 1,4-heptadiene, 1,5-heptadiene, and 1,6-heptadiene.

3. The process of claim 2 wherein the reaction is carried out at a temperature of from −90 to +50° C.

4. The process of claim 3 wherein a free radical initiator is added in an amount of from 1–25 mole % per mole of terminal alkene and the free radical initiator is a trialkyl borane.

5. The process of claim 4 wherein the free radical initiator is a triethyl borane and the reaction is carried out at a temperature of from −90 to 0° C.

6. A process for adding an SF₅ group and a bromine atom to an alkene having an internal olefinic bond selected from aliphatic and cycloaliphatic olefins represented by the formulas:

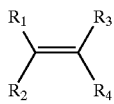

A wherein $R_1$, $R_2$, $R_3$, $R=C_{1-12}$ alkyl or substituted alkyl, aryl or substituted aryl, alkoxy, alkyl ether, alkyl ester and nitrile, with $R_2$ and $R_4$ additionally being=H or halogen atoms;

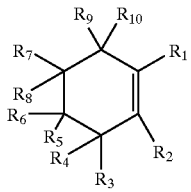

F wherein $R_1$–$R_{10}$=H, halogen atoms, $C_{1-20}$, alkyl or substituted alkyl, aryl or alkyl substituted aryl, $C_{1-10}$ alkoxy, $C_{1-10}$ alkyl ether, alkenyl, alkyl halogen, alkyl thionyl, alkyl amino, and wherein $R_9$, $R_{10}$ or $R_3$, $R_4$ also represent a carbonyl group; $R_9$ or $R_{10}$ and $R_4$ or $R_3$ also represent a bridged bicyclic compound; and wherein $R_7$ or $R_8$ and $R_5$ or $R_6$ may also represent a fused ring bicyclic or tricyclic cycloaliphatic or aromatic compound; and

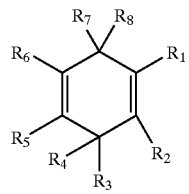

I wherein $R_1$–$R_8$=H, halogen atoms, alkyl or substituted alkyl, aryl or substituted aryl or $R_7$ or $R_8$ and $R_4$ or $R_3$ may be bridged bicyclic compounds, $R_7$ or $R_8$ and $R_5$ or $R_6$ may be fused to form bicyclic or tricyclic cycloaliphatic rings:

which comprises condensing $SF_5Br$ in said alkene and reacting said alkene with $SF_5Br$ under liquid phase conditions in the presence of a free radical initiator.

7. The process of claim 6 wherein said free radical initiator is selected from the group consisting of trialkyl borane, organic peroxide, organic azo, and ultraviolet light.

8. The process of claim 7 wherein the temperature of said reacting is from −90 to +50° C.

9. The process of claim 8 wherein the free radical initiator is triethyl borane.

10. The process of claim 9 wherein the reaction stoichiometry employs $SF_5Br$ in an amount from 1 to 1.2 moles $SF_5Br$ per mole of olefin bond in said alkene.

11. The process of claim 10 wherein triethyl borane is employed in an amount from 1–25 mol % based upon the moles of the olefin bond in said alkene to be reacted.

12. The process, of claim 11 wherein triethyl borane is employed in an amount from 5–10 mol %, based upon the moles of the olefin bond to be reacted.

13. The process of claim 9 wherein the alkene is represented by formula A and said alkenes is selected from the group consisting of pentene, hexene, heptene, octene, decene, and dodecene.

14. The process of claim 9 wherein the alkene is represented by structure F and said cyclic olefin is selected from the group consisting of: cyclohexene, cyclooctene, norbornene, dihydronaphthalene, dihydroanthracene, dihydrophenanthrene, octahydronaphthalene, dodecahydroanthracene, dodecahydrophenanthrene.

15. The process of claim 9 wherein the alkene is represented by structure I and said cyclic olefin is selected from the group consisting of 1,4-cyclohexadiene, 1,6hexahydronaphthalene, 9,13-tetrahydroanthracene.

16. A composition compound represented by the structures:

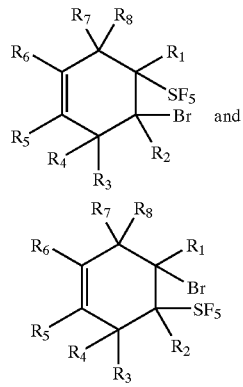

and wherein $R_1$–$R_8$=H, halogen atoms, alkyl or substituted alkyl, aryl or substituted aryl or $R_7$ or $R_8$ and $R_4$ or $R_3$ may be bridged bicyclic compounds, $R_7$ or Re and $R_5$ or $R_6$ may be fused to form bicyclic or tricyclic cycloaliphatic rings.

17. The compound of claim 16 wherein $R_1$–$R_8$ are H.

18. A compound represented by the structures:

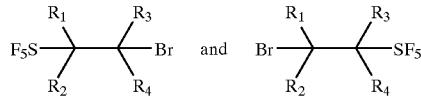

wherein $R_1$, $R_2$, $R_3$, $R_4$=$C_{1-12}$ alkyl or substituted alkyl, aryl or substituted aryl, alkoxy, alkyl ether,.alkyl ester and nitrile, with $R_2$ and $R_4$ additionally being=H or halogen atoms.

19. The compound of claim 18 wherein $R_2$ and $R_{-4}$ are $C_{3-8}$ alkyl.

20. A compound represented by the structure:

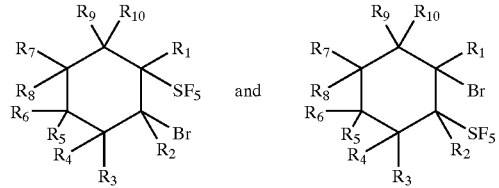

wherein $R_1$–$R_{10}$=H, halogen atoms, $C_{1-20}$, alkyl or substituted alkyl, are or alkyl substituted aryl, $C_{1-10}$ alkoxy, $C_{1-10}$ alkyl ether, alkenyl, alkyl halogen, alkyl thionyl, alkyl amino, and wherein $R_9$, $R_{10}$ or $R_3$, $R_4$ also represent a carbonyl group; $R_9$ or $R_{10}$ and $R_4$ or $R_3$ also represent a bridged bicyclic compound; and wherein $R_7$ or $R_8$ and $R_5$ or $R_6$ may also represent a fused ring bicyclic or tricyclic cycloaliphatic or aromatic compound.

21. The compound of claim 20 wherein $R_1$–$R_{10}$— are H.

* * * * *